United States Patent [19]
Ishigaki et al.

[11] Patent Number: 5,245,390
[45] Date of Patent: Sep. 14, 1993

[54] DEVICE FOR ADJUSTING OUTPUT OF IMAGE DENSITY SENSOR INCORPORATED IN IMAGE FORMING EQUIPMENT

[75] Inventors: Kouji Ishigaki, Yokohama; Yusuke Shimbo, Tokyo, both of Japan

[73] Assignee: Ricoh Company, Ltd., Tokyo, Japan

[21] Appl. No.: 811,136

[22] Filed: Dec. 20, 1991

[30] Foreign Application Priority Data

Dec. 22, 1990 [JP] Japan .................................. 2-413511

[51] Int. Cl.$^5$ ............................................ G03G 21/00
[52] U.S. Cl. .................................... 355/246; 118/663; 118/694; 355/208
[58] Field of Search .................. 355/208, 246, 245; 118/663, 689, 694

[56] References Cited

U.S. PATENT DOCUMENTS

| | | | |
|---|---|---|---|
| 4,894,685 | 1/1990 | Shoji | 355/246 |
| 5,006,896 | 4/1991 | Koichi et al. | 355/246 |
| 5,036,363 | 7/1991 | Iida et al. | 355/246 |

*Primary Examiner*—Leo P. Picard
*Assistant Examiner*—Christopher Horgan
*Attorney, Agent, or Firm*—Oblon, Spivak, McClelland, Maier & Neustadt

[57] ABSTRACT

A device incorporated in image forming equipment for adjusting the output of an image density sensor which optically senses the density of a toner image formed on a photoconductive element and representative of a reference pattern. The density sensor is made up of a light emitting element and a light-sensitive element. Thresholds divide an output range wherein the output characteristic of the sensor does not change into a plurality of subranges having the optimal output associated with the background of the photoconductive element as the center value. The sensor senses the background of the photoconductive element at predetermined intervals. Whether or not to adjust the output of the sensor is determined on the combination of the subrange where the resulting output of the sensor lies and the number of times that the former lies in the latter. The sensor output, i.e., a PWM (Pulse Width Modulation) duty to be fed to the light emitting element is changed to control the adjusted output associated with the background to the optimal value.

3 Claims, 7 Drawing Sheets

DEVICE FOR ADJUSTING OUTPUT OF IMAGE DENSITY SENSOR INCORPORATED IN IMAGE FORMING EQUIPMENT

BACKGROUND OF THE INVENTION

The present invention relates to a copier, facsimile apparatus, printer or similar image forming equipment and, more particularly, to a device incorporated in such equipment for adjusting the output of an image density sensor which optically senses the density of a toner image formed on a photoconductive element and representative of a reference pattern.

A prerequisite with image forming equipment of the type forming a toner image on a photoconductive element is that the image density and contrast be controlled to desirable levels in order to insure high image quality. The image density and contrast are effected by the toner concentration of a developer, bias voltage for development, lamp voltage for exposure, etc. To meet the above requirement, one conventional image forming apparatus forms a toner image representative of a reference pattern on a photoconductive element, determines the density of the toner image by use of an image density sensor, and controls, for example, the toner concentration or the bias voltage, as needed. However, the problem is that the output of the sensor is susceptible to the surface configuration and eccentricity of the photoconductive element (distance to the sensor), toner particles depositing on and smearing the light-sensitive surface of the sensor, a voltage saturation range particular to the conversion of the output current of the light emitting element (e.g. phototransistor) to a voltage, temperature drift, etc. It is likely, therefore, that the output of the sensor is deviated from a desirable range of output characteristic, resulting in erroneous control. In light of this, it has been customary to sense the background of the photoconductive element together with the toner image of interest, compare the difference between the resulting two outputs and the difference between their reference outputs, control the toner concentration of a developer on the basis of the result of comparison, and thereby adjust the output of the sensor against the smears caused on the light-sensitive surface of the sensor by the toner. This kind of implementation is disclosed in, for example, Japanese Patent Laid-Open Publication No. 53869/1984.

However, the above-stated scheme determines whether or not to adjust the sensor output by using a single threshold, i.e., the difference between reference outputs. This brings about a problem that even an output little different from the threshold is immediately corrected, and the correction is effected due to the influence of the eccentricity of the photoconductive element or noise. To eliminate this problem, Japanese Patent Application No. 134674/1989 teaches a procedure consisting of repetitively detecting the background of the photoconductive element a predetermined number of times while determining whether or not the resulting output lies in a predetermined range each time, and adjusting the sensor output when it is not found in the predetermined range. Since this procedure repeats the detection a predetermined number of times without exception, even a sensor output which is far different from the target output and almost saturated is apt to continuously hold until the detection has been repeated the fixed number of times, obstructing accurate control over the toner concentration and other subjects. In addition, assume equipment of the kind displaying an error when the adjusted output does not fall in the predetermined range, and a sensor extremely susceptible to, for example, temperature drift. Then, since the sensor output noticeably varies with the temperature inside the equipment, the equipment is apt to display an error frequently.

SUMMARY OF THE INVENTION

It is, therefore, an object of the present invention to provide a sensor output adjusting device for image forming equipment which is capable of adjusting the output of an image density sensor with accuracy despite a change in the distance between a photoconductive element and the sensor and a change in ambient temperature.

In accordance with the present invention, a device for adjusting the output of an image density sensor responsive to the density of a toner image formed on a photoconductive element and representative of a reference pattern comprises a counting circuit for counting the number of times that the output of the image density sensor exceeds a plurality of thresholds, and a deciding circuit for determining whether or not the output of the image density sensor should be adjusted on the basis of the combination of the thresholds and the number of times.

Also, in accordance with the present invention, an image forming apparatus comprises an image density sensor for sensing the density of a toner image formed on a photoconductive element and representative of a reference pattern, a comparing circuit for comparing the output of the image density sensor with more than three thresholds, a counting circuit responsive to the output of the comparing circuit for counting the number of times that the output of the image density sensor exceeds the threshold values on a threshold value basis, while weighting the number of times on a threshold value basis, and an adjusting circuit for adjusting the output of the image density sensor in response to a count outputted by the counting circuit.

BRIEF DESCRIPTION OF THE DRAWINGS

The above and other objects, features and advantages of the present invention will become more apparent from the following detailed description taken with the accompanying drawings in which.

DESCRIPTION OF THE PREFERRED EMBODIMENT

Figure 1:
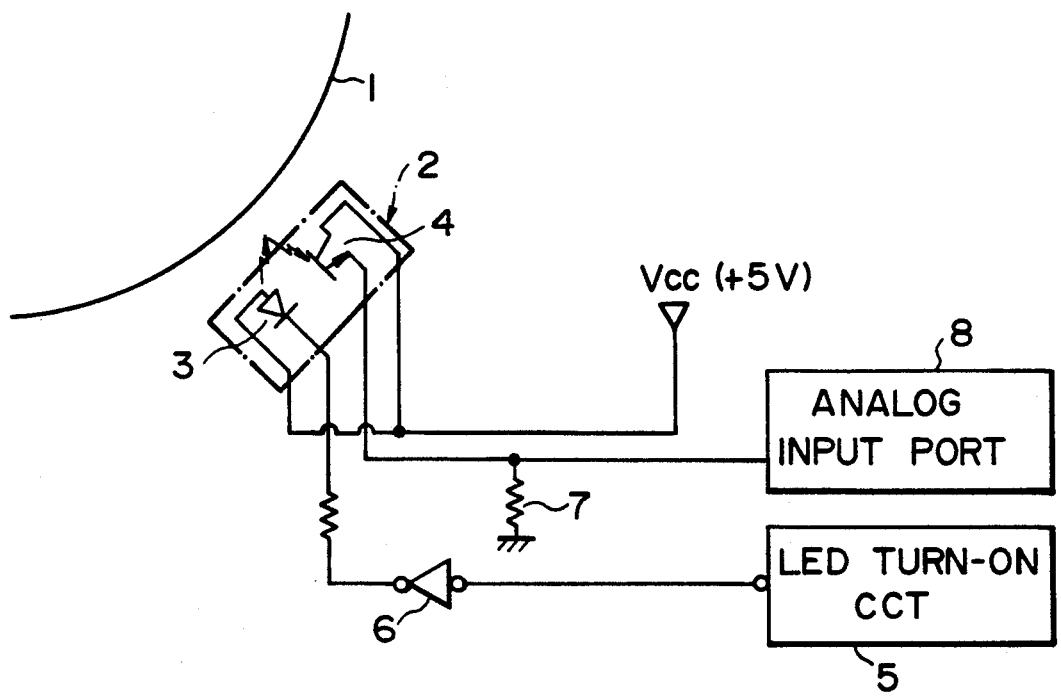
FIG. 1 is a circuit diagram showing an image density sensor to which an embodiment of the present invention is applied.

Referring to FIG. 1 of the drawings, image forming equipment to which a device embodying the present invention is applied is shown and implemented as electrophotographic equipment by way of example. As shown, the equipment has a photoconductive drum 1 and an image density sensor 2 which faces the drum 1. The image density sensor 2 is made up of an LED (Light Emitting Diode) 3 and a phototransistor 4 which serve as a light emitting element and a light-sensitive element, respectively. Conventional units for effecting an electrophotographic process are arranged around the drum 1, although not shown in the FIG. The LED 3 has an anode thereof connected to a power source line Vcc (+5 V) and has a cathode connected to an LED turn-on circuit 5 via a driver 6. The LED turn-on circuit 5 may be constituted by a timer IC (Integrated Circuit), for example. A low active PWM (Pulse Width Modulation) waveform having a resolution of several ten kHz and eight bits is applied to the LED 3. The emitter of the phototransistor 4 is connected to ground via a load resistor 7 and connected to the input terminal of an analog-to-digital (A/D) converter built in a main control board via an analog port 8 of the main control board. In this configuration, the voltage across the load resistor 7 is converted to a digital signal and fed out as the output of the image density sensor.

Toner density control using the output of the image density sensor 2 will be outlined first. A reference pattern having a reference density is provided on a glass platen outside of an area where a document is to be laid. As the reference pattern is illuminated, the resulting reflection electrostatically forms a corresponding latent image on the drum 1. A developing unit, not shown, develops the latent image to produce a toner image representative of the reference pattern. While the density of such a toner image is repetitively sensed, a change in the toner concentration of a developer stored in the developing unit is determined in terms of a change in the density of the toner image. Control over the toner concentration is effected on the basis of the change in the toner concentration. Specifically, the image density sensor 2 senses a light reflected from the toner image, i.e., reference pattern toner image formed on the drum 1 and light reflected from the background of the drum 1 where the toner image is not formed, producing an output Vsg associated with the background and an output Vsp associated with the toner image. Whether or not to supply a toner is determined on the basis of a ratio Vsp/Vsg. Such an operation for sensing the image density and determining whether or not to supply a toner is performed when the first copy is to be produced after the turn-on of the power source and every time ten copies are produced. Based on the result of this decision, the operation for supplying a toner is effected up to the instant when the reference pattern toner image should be detected again. The position of the drum 1 where the reference pattern toner image is to be formed is determined randomly by the timing for forming the reference pattern toner image. The turn-on of the LED 3 for detection and the reading of sensor output by the main control board begin at such a timing that the sensing operation begins at a background portion preceding the reference pattern toner image with respect to the direction of rotation of the drum 1. On the start of the sensing operation, the resulting data are sequentially stored in a shift register at the intervals of, for example, 4.75 msec. At the instant when an output whose level clearly distinguishes the background and the toner image (e.g. 2.5 V) has appeared, a predetermined number of data stored in the shift register and corresponding to the outputs preceding and following the above-mentioned output (some data adjoining the boundary are neglected) are averaged to produce data Vsg and Vsp. Assume that the density of the reference density toner image has lowered to an unusual degree due to an error in the developing unit or similar process unit, preventing the above-mentioned output of the distinguishing level from appearing. Then, since neither the data Vsg nor the data Vsp exists, "0" is stored in the register. In this case, a toner is supplied in a constant amount up to the time for sensing the reference pattern toner image again.

Figure 2:
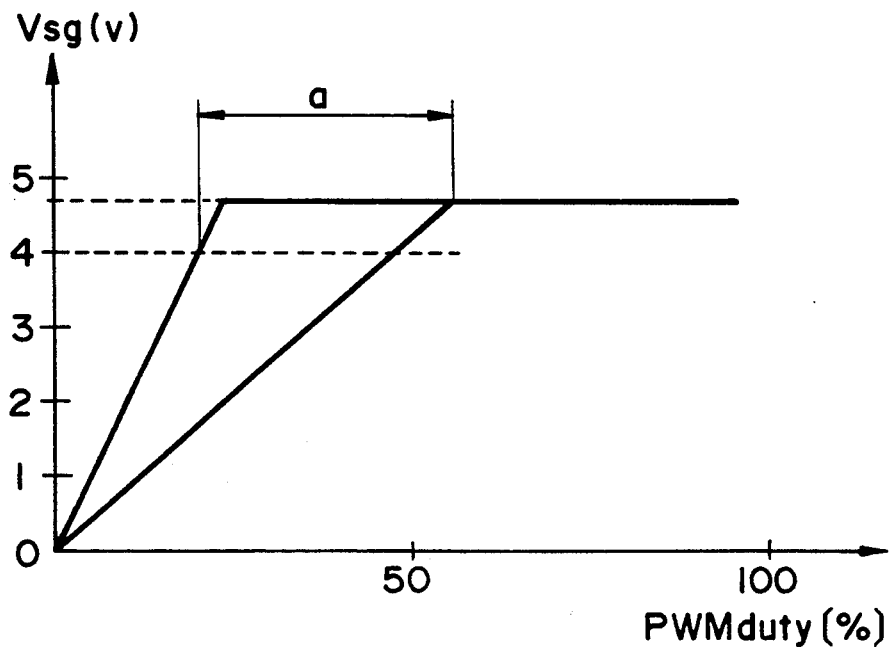
FIG. 2 is a graph indicative of the output characteristic of the sensor shown in FIG. 1.

As stated above, since the embodiment uses a ratio of the output associated with the reference pattern toner image and output associated with the background, the influence of, for example, the eccentricity of the drum 1 on the two outputs is cancelled so long as they are adequate. This is successful in controlling the toner concentration adequately. However, as shown in FIG. 2, the output of the sensor 2 has a saturation range (4.7 V in the figure) wherein it does not change despite an increase in the amount of incident light. While the abscissa of FIG. 2 indicates PWM duties which determine the quantity of light from the LED 3, let the PWM duties be regarded as the quantities of light sensed by the light-sensitive element. The saturation range prevents the density of the reference pattern toner image from being accurately detected and, therefore, obstructs adequate toner concentration control if the density is sensed at the moment when the distance between the drum 1 and the sensor 2 is reduced due to, for example, the eccentricity of the drum 1, i.e., if the output associated with the background which is relatively high coincides with the saturation range. Further, when the toner smears the light-sensitive surface of the sensor 2 to lower the sensor output, the resolution of A/D conversion is lowered to in turn reduce the accuracy of sensing operation although errors ascribable to the saturation range do not occur. In FIG. 2, the range $a$ is representative of scattering among products with respect to the time when the output begins to saturate. While such scattering causes each product to have a different inclination associated with Vsg and PWM, each product has a certain constant inclination.

In light of the above, the output of the sensor 2 is adjusted such that the output Vsg associated with the background which is relatively high does not coincide with the saturation range and lies in an advantageous range from the resolution standpoint (referred to as a range wherein the sensor characteristic does not change hereinafter).

The embodiment selects the range wherein the sensor characteristic does not change by considering the optimal value of Vsg. The optimal value of the output Vsg of the sensor 2 at Vcc+5 V is selected to be 4.0 V, for the following reasons. First, the output should preferably be as great as possible within an allowable range to enhance the resolution of A/D conversion. Second, the output fluctuates by about 0.3 V due to the eccentricity of the drum 1 and other similar causes. Third, the output of the sensor 2 begins to saturate at about 4.5 V and then fully saturates (about 4.7 V), as shown in FIG. 2. Fourth, the sensor 2 has a temperature drift of about 0.1.

Therefore, the optimal value is determined to be 4.1 V which remains when the sum of the fluctuations ascribable to the eccentricity of the drum 1 and temperature drift (tending to increase the output of the sensor 2) is subtracted from 4.5 V at which the sensor output begins to saturate, preferably 4.0 V with some margin. The output of 4.5 V is selected as the upper limit of the range wherein the sensor characteristic does not change. The lower limit of the range of interest is determined to be 3.5 V by taking account of the eccentricity of the drum 1, temperature drift, and the fluctuation ascribable to the contamination of the sensor 2 (tending to reduce the output), and so as not to reduce the resolution as far as possible.

Figure 3:
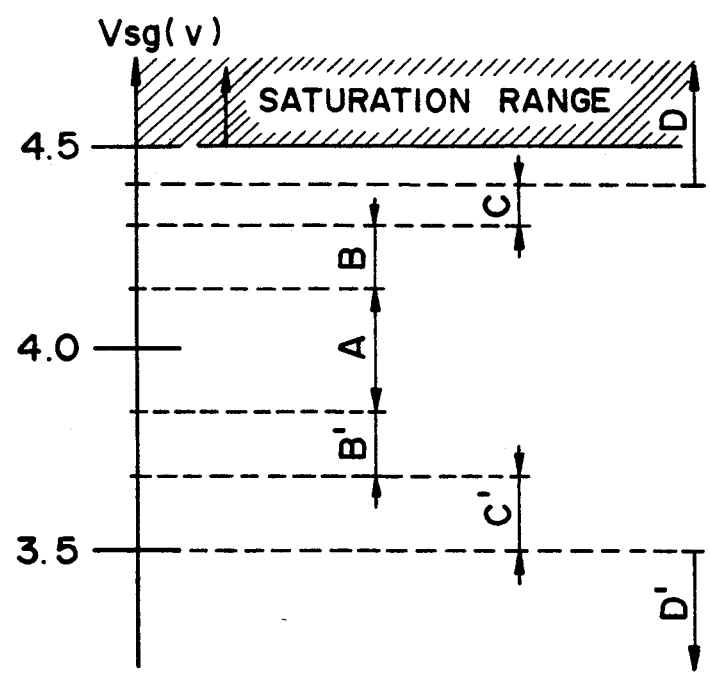
FIG. 3 shows specific thresholds for determining whether or not to adjust the output of the sensor particular to the embodiment.

Further, the embodiment subdivides the range wherein the sensor characteristic does not change, so that the output Vsg may lie in such a range without fail and the adjustment may occur slowly to eliminate overcorrection. Specifically, as shown in FIG. 3, the range above 3.5 V and below 4.5 V wherein the sensor characteristic does not change is subdivided. FIG. 3 indicates the outputs Vsg associated with the background of the drum 1 on the ordinate thereof and shows threshold levels for the decision on whether or not to effect adjustment. As shown, the range of interest is subdivided into subranges D, C, B, A, B', C' and D' by six thresholds, i.e., three thresholds above 4.0 V which is optimal and three thresholds below 4.0. The subrange A (above 3.85 V and below 4.15 V) delimited by the thresholds 2.15 V and 3.85 V each being 0.15 V distant from 4.0 V is set up in consideration of the fluctuation of 0.3 V ascriable to the eccentricity of the drum 1 and which is most probable. When the output Vsg lies in the subrange A, no adjustment is effected. The subrange B delimited by the threshold 4.15 V and the threshold 4.30 V (above 4.15 V and below 4.30 V) is defined in consideration of greater eccentricity of the drum 1. The subrange C delimited by the threshold 4.30 V and the threshold 4.40 V (above 4.30 V and below 4.40 V) is determined mainly in consideration of the fluctuation ascribable to temperature drift. The subrange D is higher than the threshold 4.40 V. Likewise, the subranges B', C' and D' which are lower than the optimal 4.0 V are delimited by thresholds 3.70 V and 3.50 V and selected mainly in consideration of the fluctuation ascribable to the smears of the sensor 2. Regarding the subrange B, adjustment is effected if the output Vsg is determined to lie in the subrange B or the subrange C three consecutive times. Regarding the range C, adjustment is effected when the output Vsg is determined to lie in the subrange D two consecutive times. Further, regarding the subrange D, adjustment is effected when the output Vsg is determined to lie in the subrange D once. Likewise, regarding the subranges B', C' and D', adjustment is performed when the output Vsg is determined to lie in the subrange B' or the subrange C' three consecutive times, to lie in the subrange D' two consecutive times, or to lie in the subrange D' once.

In the above-described manner, whether or not to perform adjustment is determined on the basis of the level and threshold of the output Vsg and the number of times that the output Vsg has exceeded the threshold. The PWM duty to be fed to the LED 3 is changed by the output Vsg in such a manner as to control the output Vsg to 4.0 V which is optimal, whereby the output of the image density sensor 2 is adjusted.

Specific control over the adjustment of the sensor output will be described with reference to FIGS. 3-7.

Figure 5:
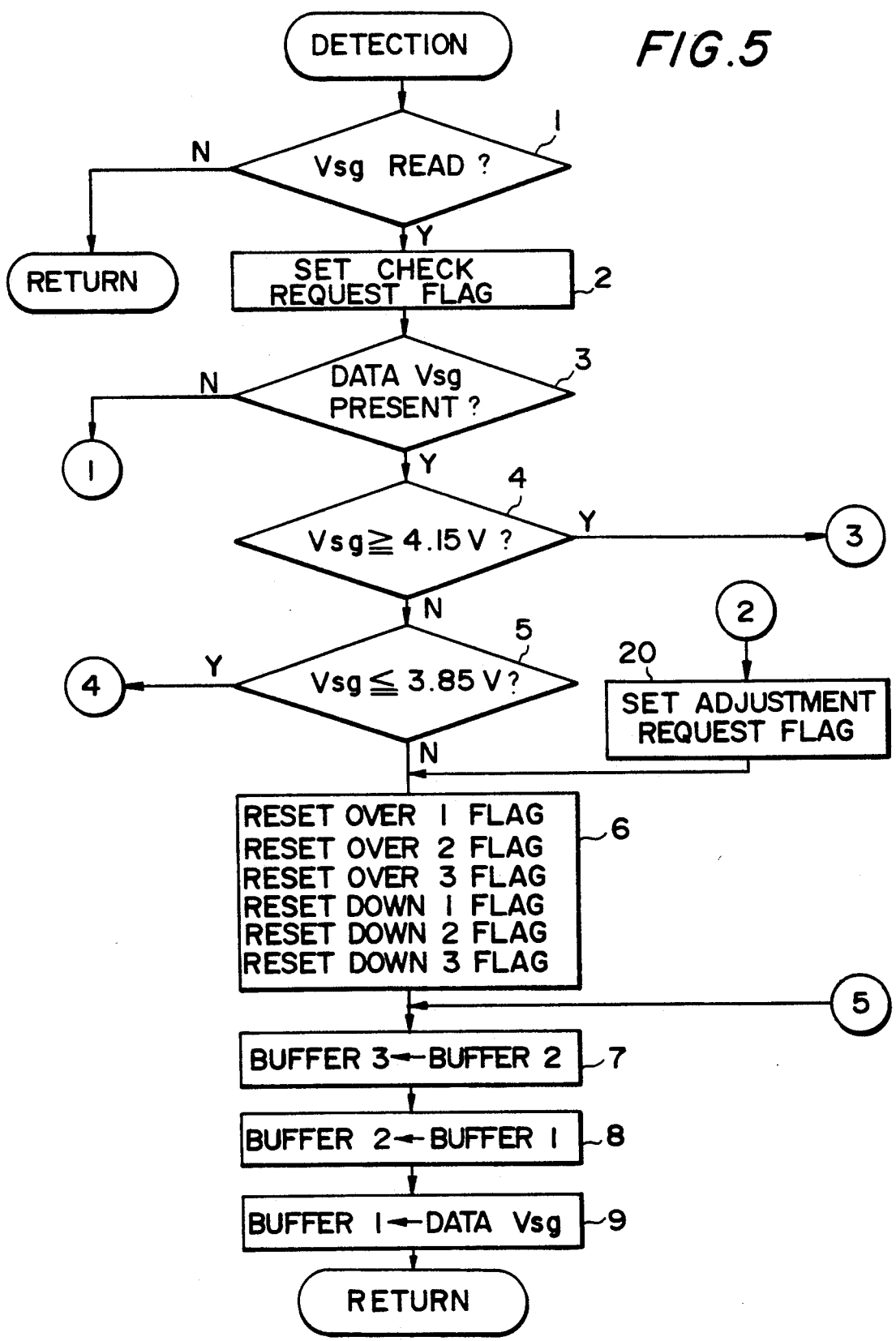
FIG. 5 is a flowchart representative of part of control for adjusting the output of the sensor.
Figure 6:
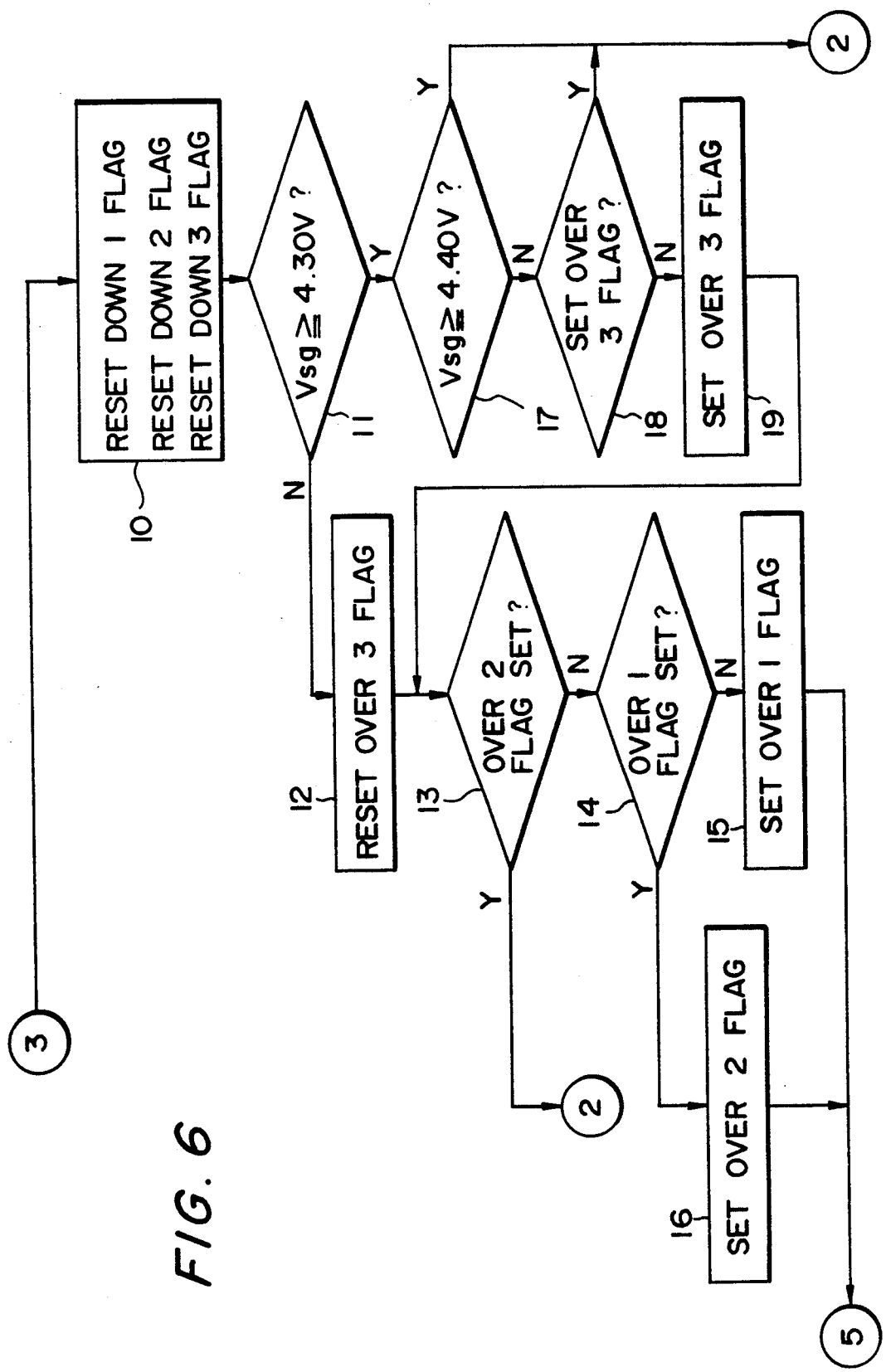
FIG. 6 is a flowchart showing another part of the control.
Figure 7:
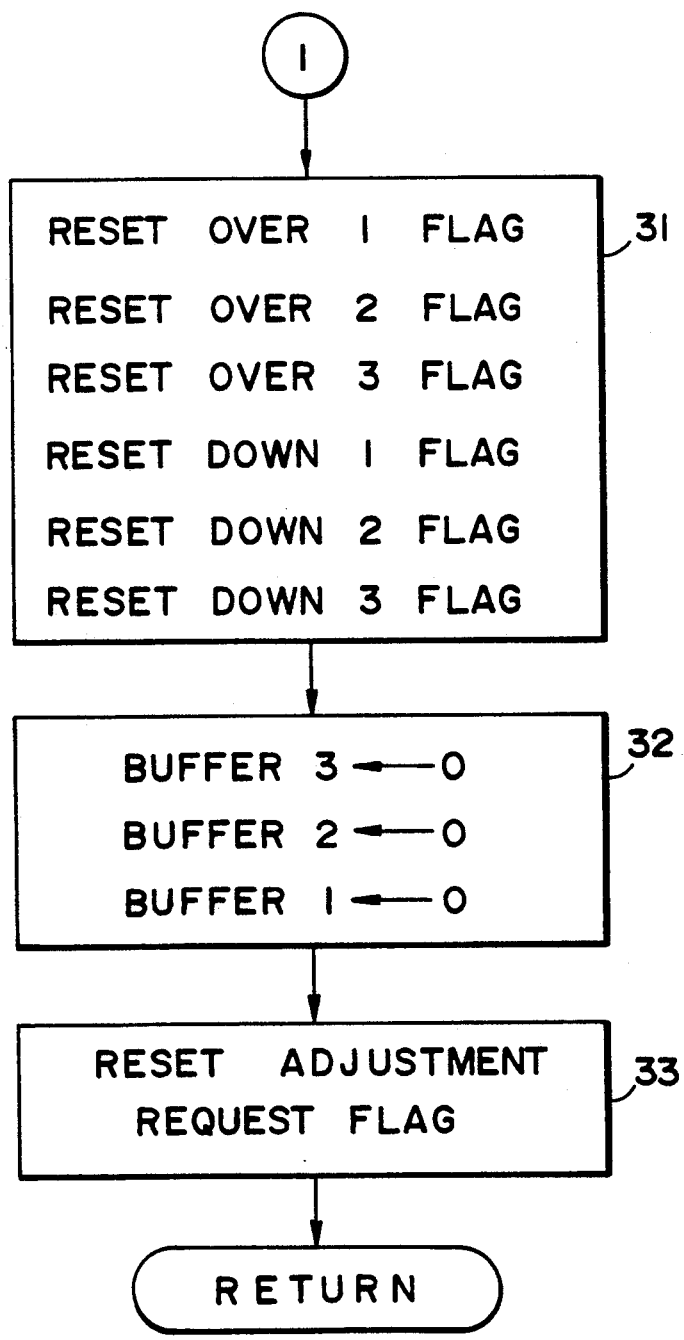
FIG. 7 is a flowchart showing still another part of the control.

First, the control over the decision as to whether or not to effect adjustment will be described with reference to FIG. 5. In FIG. 5, whether or not the output Vsg has been read is determined (step 1). For this purpose, use may be made of a decision request flag which is set when the sensor 2 is turned off after having been turned on to produce outputs Vsg and Vsp every predetermined number of times. If the answer of the step 1 is positive, the decision request flag is reset (step 2), and then whether or not output data Vsg is present is determined (step 3). Assume that data Vsg is absent (N, step 3) due to an error in the developing unit or similar process unit, as stated earlier. Then, the operation is transferred to a step 31 shown in FIG. 7 for resetting an over 1 flag, an over 2 flag, an over 3 flag, a down 1 flag, a down 2 flag and a down 3 flag. These flags are used to determine the number of times that the output Vsg has been continuously found in the range B or C. Subsequently, a buffer 3, a buffer 2 and a buffer 1 are reset (step 32). These buffers serve to store the outputs Vsg. An adjustment request flag is reset (step 33). The adjustment request flag is set when adjustment which will be described is necessary.

If data Vsg is present (Y, step 3), whether or not it lies in the subrange A is determined (steps 4 and 5). If the data Vsg lies in the subrange A (N, steps 4 and 5), the flags are reset as in the step 31, FIG. 7, (step 6). Then, the buffer 3 is updated by the output data Vsg stored in the buffer 2 (step 7). Likewise, the buffer 2 is updated by the data Vsg stored in the buffer 1 (step 8), and then the buffer is updated by the latest data Vsg (step 9). If the data Vsg is greater than the subrange A (Y, step 4), the operation is transferred to a step 10 of FIG. 6 for resetting the down 1 flag, down 2 flag and down 3 flag. Subsequently, which of the subranges B, C and D has the data Vsg therein is determined (steps 11 and 17). If the data lies in the subrange D (Y, step 17), the operation is immediately transferred to a step 20 of FIG. 5 to set an adjustment request flag which will be described. This is followed by steps 6–9 for updating the buffers 1, 2 and 3 in the above-stated manner.

If the data Vsg lies in the subrange B or C (N, step 11 or 17), the over 1 flag, over 2 flag and over 3 flag are used to reference the result of immediately preceding Vsg detection or, if necessary, the results of two preceding Vsg detections to thereby select particular processing. Specifically, when the output Vsg lying in the subrange A sequentially increases to enter the subrange B for the first time as determined by the detection, steps 11-15 are executed since all of the over 1 flag, over 2 flag and over 3 flag have been reset. In the step 15, the over flag 1 is set, and then in steps 7-9 of FIG. 5 the buffers 1, 2 and 3 are updated. When the output Vsg is again determined to lie in the subrange B by the next detection, steps 14-16 are executed since the over 1 flag has already been set. In the step 16, the over 2 flag is set, and then the steps 7-9 are executed. In the event of the next Vsg detection, since the over 2 flag has already been set, steps 13-20 are executed to set the adjustment request flag (steps 11, 12, 13 and 20 or steps 17, 18, 19, 13 and 20) even if the output Vsg lies in the subrange B or C. Further, all of the over 1 flag, down 1 flag and other similar flags are reset (step 6). Then, all the buffers are updated (steps 7-9).

Assume that the output Vsg following the output Vsg which has been determined to lie in the subrange B for the first time lies in the subrange C. Then, since the over 1 flag has already been set, the steps 17-19 are again executed. In the step 19, the over 3 flag is set. Subsequently, the over 2 flag is set (step 16), followed by the steps 7-9. When the next Vsg detection indicates that Vsg lies in the subrange B, the steps 11-13 are executed. At this instant, since the over 2 flag has already been set, the adjustment request flag is set (step 20). On the other hand, if the output Vsg lies in the subrange C, meaning that the over 2 flag has been set, the adjustment request flag is set (steps 17, 18 and 20). This is again followed by the steps 6-9.

When the output Vsg lying in the subrange A sharply increases to enter the subrange C for the first time, the steps 17-19 are executed. Specifically, the over 3 flag is set (step 19). Since the over 1 flag and over 2 flag have been reset, the over 1 flag is set (step 15), followed by the steps 7-9. When the next Vsg detection also indicates that Vsg lies in the subrange C, the adjustment request flag is set (steps 17, 18 and 20) since the over 3 flag has already been set. This is followed by the steps 6-9. When the output Vsg following Vsg having been determined to lie in the subrange C for the first time lies in the subrange B, the program advances from the step 11 to the step 12 for resetting the over 3 flag, and then the steps 13-16 are executed. Specifically, the step 16 sets the over 2 flag and is followed by the steps 7-9. In the event of the next Vsg detection, since the over 2 flag has been set and the over 3 flag has been reset, the operation is transferred from the step 13 to the step 20 to set the adjustment request flag (steps 1, 12, 13 and 20 or steps 17, 18, 19, 13 and 20) even if Vsg is determined to lie in the subrange B or C, as as been the case with the continuous detection of Vsg in the subrange B. Thereafter, the steps 6-9 are executed.

The step 20 for setting the adjustment request flag is executed only when Vsg is determined to lie in the subrange B or C three or two consecutive times, as stated above. If Vsg is found in a subrange other than B and C during such successive detections, all of the over 1 flag and other similar flags are reset (step 6 and step 21, FIG. 8). As a result, all the results accumulated by the over 1 flag and other flags are cleared.

Figure 8:
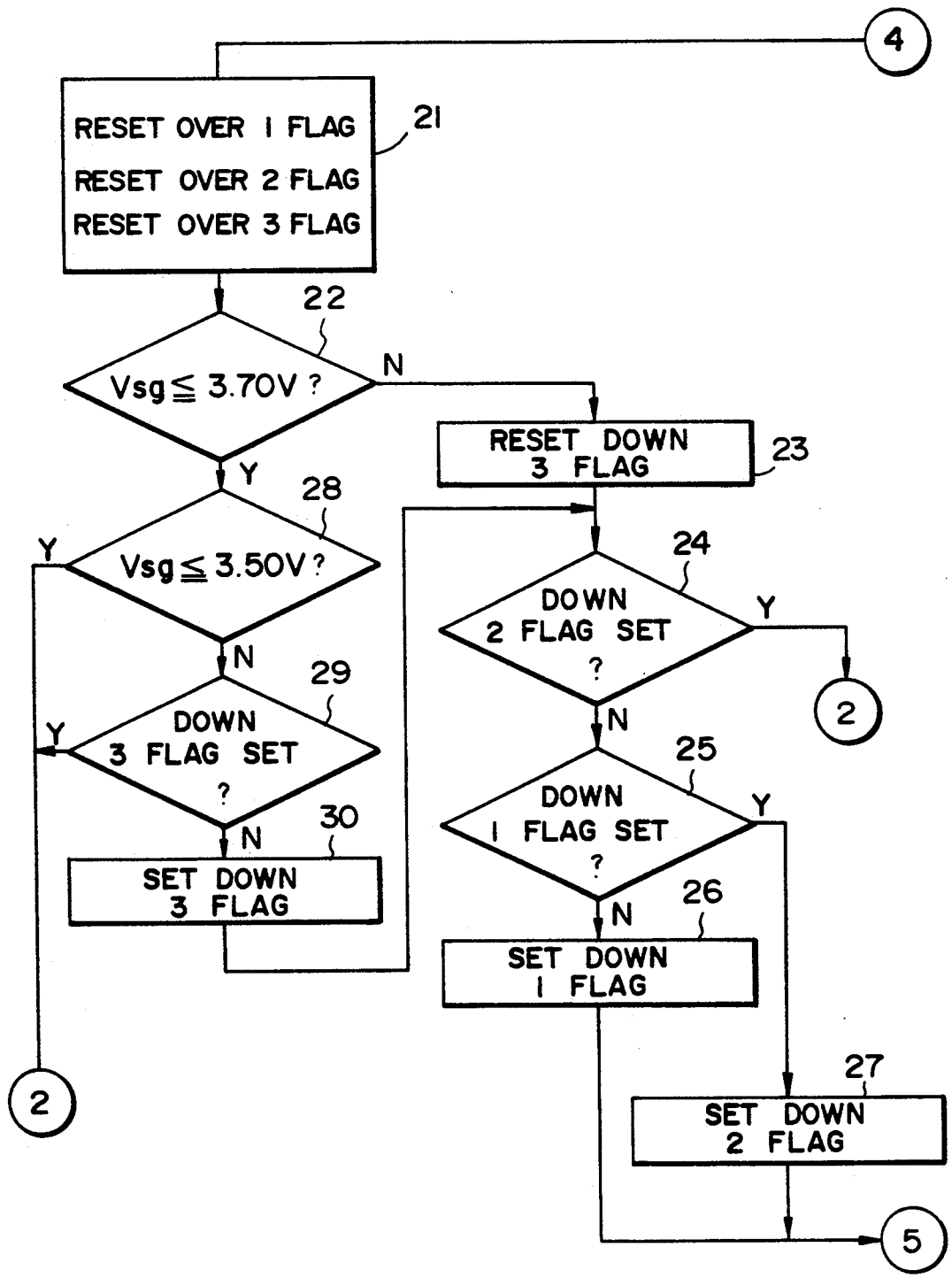
FIG. 8 is a flowchart showing a further part of the control.

When the data Vsg is smaller than the subrange A (Y, step 5, FIG. 5), the operation is transferred to a step 21, FIG. 8, for resetting the over 1 flag and other similar flags. Thereafter, which of the subranges B', C' and D' has the data Vsg therein is determined (steps 22 and 28). If the data Vsg lies in the subrange D', the adjustment request flag is set (step 20, FIG. 5), and then the steps 6-9 are executed, as with the data Vsg lying in the subrange D. If the data Vsg lies in the subrange B' or C' (N in step 22 or 28), the down 1 flag, down 2 flag and down 3 flag are used to reference the result of immediately preceding Vsg detection or, if necessary the results of two preceding Vsg detections so as to select particular processing, as with the data Vsg lying in the subrange B or C. In this case, the down 1 flag and other similar flags correspond to the over 1 flag and other similar flags, the steps 21-27 of FIG. 8 correspond to the steps 10-16 of FIG. 6, and the steps 28-30 of FIG. 8 correspond to the steps 17-19 of FIG. 6.

Figure 4:
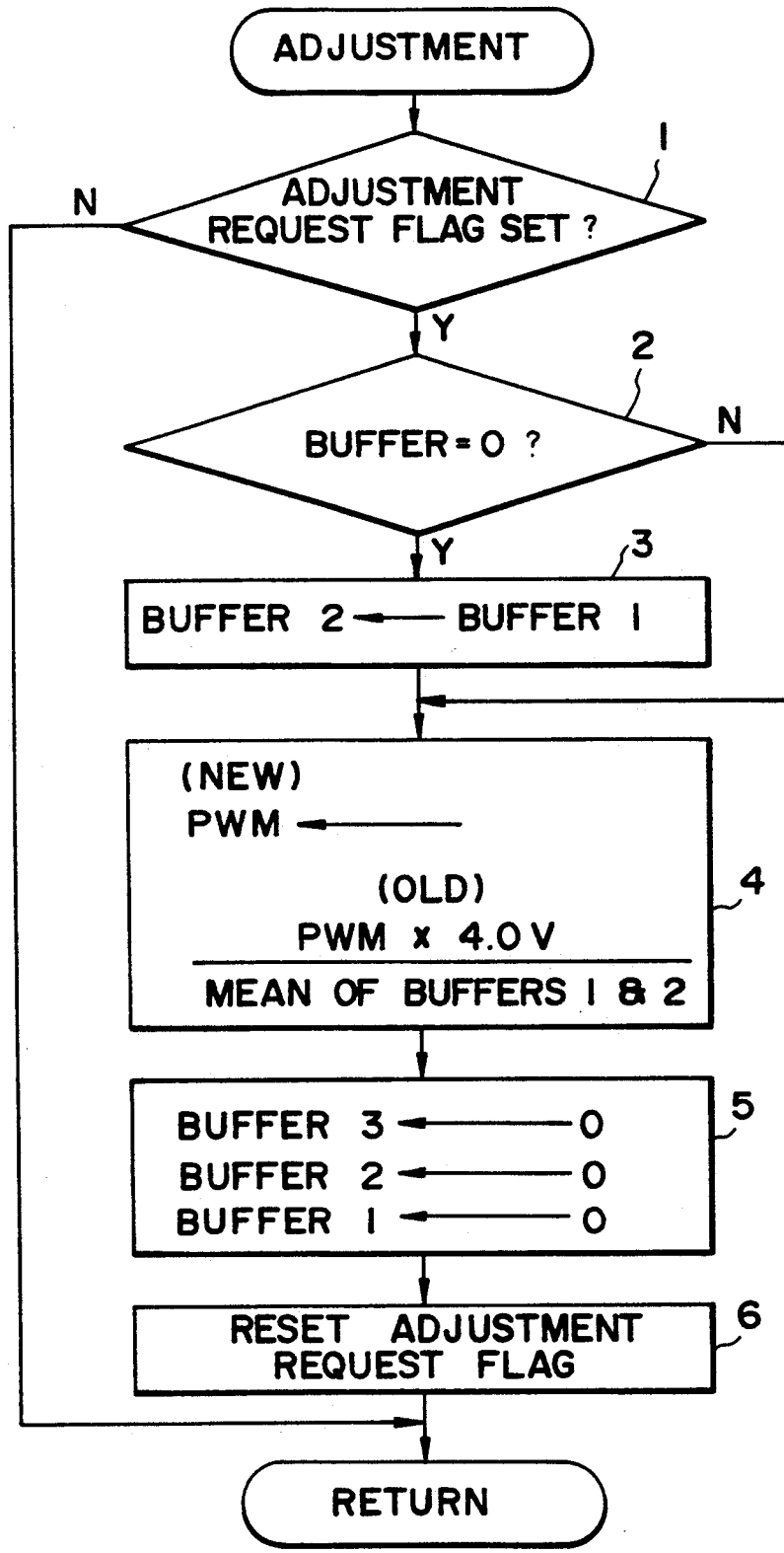
FIG. 4 is a flowchart demonstrating a control procedure for the adjustment of the output of the sensor.

How to adjust the sensor output will be described with reference to FIG. 4. As shown, whether or not the adjustment request flag is set is determined (step 1) and, if it is set, whether or not the buffer 2 stores data is determined (step 2). Since the buffer 2 usually stores data, PWM is calculated (step 4). Based on the fact that Vsg and PWM have a linear relation shown in FIG. 2, the embodiment calculates PWM (new) for controlling the output Vsg to 4.0 V which is optimal. To reduce the influence of the eccentricity of the drum 1, the embodiment uses a mean value of the latest data Vsg stored in the buffer 1 and the immediately preceding Vsg data as the current output. If Vsg and PWM do not have such a linear relation, PWM which causes Vsg to coincide with 4.0 V may be calculated by using the maximum value of $\Delta Vsg/\Delta PWM$, i.e., inclination of the tangent of the characteristic curve as a reference. This is successful in reducing the variation of PWM from the current PWM, compared to the case wherein other $\Delta Vsg/\Delta PWM$ are used, and thereby eliminating overadjustment. Subsequently, the buffers 1, 2 and 3 are cleared (step 5), and then the adjustment request flag is reset (step 6). When the output Vsg lies in the subrange D or D', the adjustment request flag is immediately set while the buffers 1, 2 and 3 are updated. Hence, if Vsg is found in the subrange D or D' by the first Sg detection, i.e., in the absence of past results, data is absent in the buffer 2. Therefore, when the buffer 2 is determined to be empty, data stored in the buffer 1 is also written to the buffer 2 (step 3).

As stated above, the illustrative embodiment clearly defines an output range wherein the output characteristic of the image density sensor does not change, and subdivides such an output range so that the adjustment may occur slowly targeting the center of the output range, thereby eliminating overadjustment (excessively high outputs and excessively low outputs). Hence, the toner concentration can be controlled to a level which lies in a range wherein the sensor output characteristic is stable and which is least susceptible to disturbances (surface configuration and eccentricity of drum and temperature drift), insuring stable image density. The adjustment does not entail any adverse effect (overadjustment). When the image forming apparatus has a nonvolatile RAM or similar storage, the PWM value of the LED may be stored therein after adjustment. The flags and buffers 1-3 may also be stored in such a storage, if possible. This will allow the detection and adjustment to be performed without being influenced by the turn-on or turn-off of the power source. When the sensor is controlled by a plurality of CPUs, the CPU for practicing the present invention may send the result of adjustment and other data to the other CPUs in a particular format (serial communication).

In summary, in accordance with the present invention, an image density sensor senses the background of a photoconductive element where a toner image is absent, and the resultant output of the sensor is compared with thresholds which subdivide a predetermined output range including an optimal output value into more than four subranges. Such a sensing and comparing procedure is repeated. Whether or not to adjust the sensor output is determined on the basis of the subrange where the sensor output lies and the number of times that the sensor output has been found in such a range. The invention, therefore, adequately adjusts the sensor output despite a change in the distance between the photoconductive element and the sensor or a change in ambient temperature.

Various modifications will become possible for those skilled in the art after receiving the teachings of the present disclosure without departing from the scope thereof.

What is claimed is:

1. A device for adjusting the output of an image density sensor responsive to the density of a toner image formed on a photoconductive element and representative of a reference pattern, said device comprising:

counting means for counting the number of times that the output of said image density sensor exceeds a plurality of thresholds; and deciding means for determining whether or not the output of said image density sensor should be adjusted on the basis of the combination of said thresholds and said number of times.

2. An image forming apparatus comprising:

image density sensing means for sensing the density of a toner image formed on a photoconductive element and representative of a reference pattern;

comparing means for comparing the output of said image density sensing means with more than three thresholds;

counting means responsive to the output of said comparing means for counting the number of times that said output of said image density sensing means exceeds said threshold values on a threshold value basis, while weighting said number of times on a threshold value basis; and adjusting means for adjusting the output of said image density sensing means in response to a count outputted by said counting means.

3. A device for adjusting, to a desired level, an output level of an image density sensing means responsive to the density of a toner image formed on a photoconductive element and representative of a reference pattern, said device comprising:

first comparing means for comparing the output of said sensing means with a first threshold level;

second comparing means for comparing the output of said sensing means with a second threshold level, wherein a first difference between said desired output level and said second threshold level is greater than a second difference between said desired output level and said first threshold level;

first counting means, responsive to the output of said first comparing means, for counting the number of times that said output level of said sensing means exceeds said first threshold level;

second counting means, responsive to the output of said second comparing means, for counting the number of times that said output level of said sensing means exceeds said second threshold level;

adjusting means for adjusting the output level of said sensing means when an output of said first counting means reaches a first predetermined value or when the output of said second counting means reaches a second predetermined value smaller than said first predetermined value.

* * * * *